United States Patent [19]

Brown et al.

[11] Patent Number: 4,692,262

[45] Date of Patent: Sep. 8, 1987

[54] SKIN CLEANSER CAPABLE OF SOFTENING AND REMOVING SMEGMA

[76] Inventors: Robert L. Brown, 3917 Evergreen, Irving, Tex. 75061; Elizabeth C. Stewart, No. 6 Pinecreek La., Houston, Tex. 77055

[21] Appl. No.: 908,697

[22] Filed: Sep. 18, 1986

[51] Int. Cl.4 ................................................. C11D 3/48
[52] U.S. Cl. .................................... 252/106; 252/173; 252/550; 252/559; 252/DIG. 5; 424/149; 514/358
[58] Field of Search ........... 252/106, 107, 173, 174.21, 252/542, 550, 559, DIG. 5, DIG. 14; 424/149; 514/358

[56] References Cited

U.S. PATENT DOCUMENTS 3,147,124  9/1964  Wentworth .......................... 424/149
3,787,566  1/1974  Gauvreau ............................ 514/358

FOREIGN PATENT DOCUMENTS 188316  9/1985  Japan .

*Primary Examiner*—Paul Lieberman
*Assistant Examiner*—Hoa Van Le
*Attorney, Agent, or Firm*—Pravel, Gambrell, Hewitt, Kimball & Krieger

[57] ABSTRACT

A cleansing composition capable of removing smegma comprises in an aqueous solution a cleansing agent comprising a mixture of surface active agents in the indicated amounts as follows:

(i) from a trace to 0.2% by weight, based on the total weight of said composition, as an active material of cetylpyridinium chloride, (ii) from a trace to not more than 20 ppm chlorine dioxide, (iii) from a trace to 1% by weight, based on the total weight of said composition as an active material, of polyoxyethylene (20) sorbitan monosterate, and (iv) sodium lauryl sulfate from a trace to 2%.

4 Claims, No Drawings

SKIN CLEANSER CAPABLE OF SOFTENING AND REMOVING SMEGMA

BACKGROUND OF THE INVENTION

1. Field of the Invention

The present invention relates to a cleansing composition suitable for use as a topical cleanser for removing smegma from human skin.

2. Description of the Prior Art

There have been proposed several cleaning agents for cleaning and/or removing oily secretions from human skin, particularly the facial area, such as U.S. Pat. No. 3,988,255 and U.S. Pat. No. 4,495,079 as well as U.S. Pat. No. 4,287,101 which discloses a detergent composition for removing sebum or smegma from soil spots in fabrics. None of these, however, are considered suitable for topical application to human skin and particularly where traces of such material may be ingested.

SUMMARY OF THE INVENTION

The present invention relates to a new and improved cleaning composition for removing accumulations of smegma from the surface of human skin and particularly from the skin in the genital area. Because of the waxy or cheese-like nature of smegma, which is secreted from sebaceous glands, ordinary bath soap is not always effective in the complete removal of this material. Also, because of the fatty constituents formed in smegma, it is a host for the growth of a mycobacteria. This invention will also act as a deodorizer.

The present invention is effective as a topical cleanser suitable for removal of smegma from human skin and, because of the particular constituents is hypoallergenic and non-irritating to the skin as well as cavities in the human body.

An object of the present invention is to provide a skin cleanser which combines cleansing agents which are hypoallergenic and non-irritating to the human skin, particularly in sensitive areas such as about the genitals and which is suitable for human ingestion and is germicidal, tuberculocidal, fungicidal and virocidal. Yet another object is to provide a skin cleanser capable of removing smegma from the genital area without irritating the skin which in that area is particularly sensitive.

The present invention provides a skin cleanser for topical application which is capable of softening and removing smegma from human skin without causing irritation to the treated area or to body cavities. The preferred cleanser is a mixture of water with the following amounts of cleansing agents:

(i) from a trace to 0.2% by weight, based on the total weight of said composition, as an active material of cetylpyridinium chloride, (ii) from a trace to not more than 50 ppm chlorine dioxide, (iii) from a trace to 1% by weight, based on the total weight of said composition as an active material, of polyoxyethylene sorbitan monostearate (tween-60).

Also, artificial coloring or flavors or natural, non-sugar sweetener may be added if desired, and (iv) sodium lauryl sulfate from a trace to 2%.

DESCRIPTION OF THE PREFERRED EMBODIMENT

The genital skin cleanser formulation of this invention may be in the form of a lotion, spray, cream, gel, or foam, as desired. The cleansing function of the composition is provided principally by the active ingredients of cetylpyridinium chloride sodium lauryl sulfide, chlorine dioxide, and polysorbate 60 (tween 60) which is a polyoxyethylene sorbitan monosterate.

It is also possible to include small amounts of other additives such as fragrances, flavors, sweeteners, coloring agents or foaming agents or the like.

This cleanser is to be applied topically to the genital area to clean such areas including the removal of accumulated smegma and the microbiological organisms which may be accumulated therewith. Smegma provides a culture medium or host material for such microbiological organisms. It will be appreciated that the cleanser composition of the present invention is hypoallergenic and non-irritating both to the human skin and to the tissue forming body cavities (mucosal lining tissue).

What is claimed is:

1. A skin cleanser capable of softening and removing smegma and microbiological organisms which may be associated therewith from the human skin which comprises a mixture containing:

from a trace to 0.2% by weight, based on the total weight of said composition, as an active material of cetylpyridinium chloride, from a ttace to not more than 20 ppm chlorine dioxide, from a trace to 2% by weight, based on the total weight of said composition as an active material, of polyoxyethylene (20) sorbitan monostearate; and from a trace to not more than 2% sodium lauryl sulfate.

2. The invention of claim 1 wherein the mixture is suitable for oral ingestion.

3. The invention of claim 1 wherein the mixture is non-irritating to the skin in the genital area or the body cavities.

4. A topical skin deodorizer reducing or eliminating the odor from human skin caused by accumulation of smegma and microbiological organisms which may be associated therewith which deodorizer comprises a mixture containing:

from a trace to 0.2% by weight, based on the total weight of said composition, as an active material of cetylpyridinium chloride, from a trace to not more than 20 ppm chlorine dioxide, from a trace to 2% by weight, based on the total weight of said composition as an active material, of polyoxyethylene (20) sorbitan monostearate; and from a trace to not more than 2% sodium lauryl sulfate.

* * * * *